US009562062B2

(12) United States Patent
Lee et al.

(10) Patent No.: US 9,562,062 B2
(45) Date of Patent: Feb. 7, 2017

(54) LIGAND COMPOUND, ORGANIC CHROMIUM COMPOUND, CATALYST SYSTEM FOR ETHYLENE OLIGOMERIZATION, AND METHOD FOR ETHYLENE OLIGOMERIZATION USING THE SAME

(71) Applicant: LG CHEM, LTD., Seoul (KR)

(72) Inventors: Sung Min Lee, Daejeon (KR); Yong Ho Lee, Daejeon (KR); Min Seok Cho, Daejeon (KR); Seok Pil Sa, Daejeon (KR); Ki Soo Lee, Daejeon (KR)

(73) Assignee: LG Chem, Ltd, Seoul (KR)

( * ) Notice: Subject to any disclaimer, the term of this patent is extended or adjusted under 35 U.S.C. 154(b) by 0 days.

(21) Appl. No.: 14/760,969

(22) PCT Filed: Sep. 26, 2014

(86) PCT No.: PCT/KR2014/009046
§ 371 (c)(1),
(2) Date: Jul. 14, 2015

(87) PCT Pub. No.: WO2015/046965
PCT Pub. Date: Apr. 2, 2015

(65) Prior Publication Data
US 2015/0361118 A1 Dec. 17, 2015

(30) Foreign Application Priority Data

Sep. 30, 2013 (KR) .................. 10-2013-0116496
Sep. 25, 2014 (KR) .................. 10-2014-0128391

(51) Int. Cl.
*C07F 9/09* (2006.01)
*C07F 11/00* (2006.01)
*B01J 31/18* (2006.01)
*C07F 9/50* (2006.01)
*B01J 23/26* (2006.01)
*C07F 9/46* (2006.01)
*B01J 31/14* (2006.01)
*C07C 2/32* (2006.01)

(52) U.S. Cl.
CPC .............. *C07F 9/5027* (2013.01); *B01J 23/26* (2013.01); *B01J 31/143* (2013.01); *B01J 31/188* (2013.01); *C07C 2/32* (2013.01); *C07F 9/46* (2013.01); *C07F 11/00* (2013.01); *C07F 11/005* (2013.01); *B01J 2231/20* (2013.01); *B01J 2531/62* (2013.01); *C07C 2531/14* (2013.01); *C07C 2531/18* (2013.01)

(58) Field of Classification Search
CPC ....... C07F 9/5027; C07F 11/00; C07F 11/005; B01J 31/143; B01J 31/188; C07C 2/32
USPC ............... 556/17; 585/523; 564/12; 502/117
See application file for complete search history.

(56) References Cited

U.S. PATENT DOCUMENTS

| | | | |
|---|---|---|---|
| 5,557,023 | A | 9/1996 | Somogyvari et al. |
| 2006/0036049 | A1 | 2/2006 | Zhao et al. |
| 2007/0232481 | A1 | 10/2007 | Zhang et al. |
| 2011/0015061 | A1 | 1/2011 | Gao et al. |
| 2012/0172645 | A1 | 7/2012 | Sydora |

FOREIGN PATENT DOCUMENTS

| | | |
|---|---|---|
| CN | 1727367 A | 2/2006 |
| CN | 101032695 A | 9/2007 |
| CN | 101511851 A | 8/2009 |
| CN | 102040624 A | 5/2011 |
| CN | 103285926 A | 9/2015 |
| JP | 2007056002 A | 3/2007 |
| JP | 2010-195905 A | 9/2010 |
| KR | 1020090121395 A | 11/2009 |
| KR | 1020100046170 A | 5/2010 |
| KR | 1020120004985 A | 1/2012 |
| KR | 1020120138309 A | 12/2012 |
| KR | 1020130105126 A | 9/2013 |
| WO | 2005123633 A1 | 12/2005 |
| WO | 2011130822 A1 | 10/2011 |
| WO | 2011140629 A1 | 11/2011 |

OTHER PUBLICATIONS

Kayan et al., Transition Met. Chem., vol. 36, No. 5, pp. 513-520 (2011).*
C-Substituted Bis(diphenylphosphino)methane-Type Ligands for Chromium-Catalyzed Selective Ethylene Oligomerization Reactions, Organometall ics, 2009, vol. 28, pp. 4613-4616.
Inorganica chimica Acta, 385 (2012) 164-169 "Synthesis and reactivity of bis(diphenylphosphino)amine ligands and theirapplication in Suzuki cross-coupling reactions".
Zhang et al.: "Synthesis of Diphenylphosphinoamine Ligands and Their Catalytic Performance for Ethylene Tetramerization with Cr (III) Compounds", Chinese Journal of Catalysis, vol. 27, No. 5, May 2006, pp. 416-420, with English Abstract.
Zhao Tan: "Advance in research of bis(Phosphine) amine ligand in Cr-based catalyst for ethylene tetramerization", Petrochemical Technology & Application, vol. 28, No. 5, Sep. 2010, pp. 429-442, with English Abstract.
Sarcher et al.: "Bi-and tetrametallic complexes of the noble metals with PNP-ligands", Journal of Organometallic Chemistry 751 (2014) pp. 343-350.

* cited by examiner

*Primary Examiner* — Porfirio Nazario Gonzalez
(74) *Attorney, Agent, or Firm* — Dentons US LLP

(57) ABSTRACT

The present invention relates to a ligand compound, a catalyst system for ethylene oligomerization, and a method for ethylene oligomerization using the same. The catalyst system for ethylene oligomerization according to the present invention not only has excellent catalytic activity but also shows more improved liquid olefin selectivity, and enables more effective preparation of an alpha-olefin through the oligomerization of ethylene because it is particularly possible to control the selectivity to 1-hexene or 1-octene.

15 Claims, No Drawings

LIGAND COMPOUND, ORGANIC CHROMIUM COMPOUND, CATALYST SYSTEM FOR ETHYLENE OLIGOMERIZATION, AND METHOD FOR ETHYLENE OLIGOMERIZATION USING THE SAME

This application is a National Stage Application of International Application No. PCT/KR2014/009046, filed Sep. 26, 2014, and claims the benefit of Korean Application No. 10-2013-0116496, filed Sep. 30, 2013, and Korean Application No. 10-2014-0128391, filed Sep. 25, 2014, all of which are hereby incorporated by reference in their entirety for all purposes as if fully set forth herein.

TECHNICAL FIELD

The present invention relates to a ligand compound, an organic chromium compound, a catalyst system for ethylene oligomerization including the ligand compound or the organic chromium compound, and a method for ethylene oligomerization using the same.

BACKGROUND OF ART

Linear alpha-olefins such as 1-hexene, 1-octene, and the like are used in a cleaner, a lubricant, a plasticizer, and so on, and particularly, are widely used as a comonomer for adjusting the density of a polymer during the preparation of linear low density polyethylene (LLDPE).

Such linear alpha-olefins have been mostly prepared through a shell higher olefin process. However, since the method synthesizes alpha-olefins of various lengths together according to Schultz-Flory distribution, there is an inconvenience of needing an additional separation process in order to obtain a specific alpha-olefin.

In order to resolve this problem, a method of selectively synthesizing 1-hexene through a trimerization reaction of ethylene or a method of selectively synthesizing 1-octene through tetramerization of ethylene were suggested. Further, various studies on catalysts enabling such selective oligomerization of ethylene are being progressed.

DETAILED DESCRIPTION OF THE INVENTION

Technical Problem

It is an aspect of the present invention to provide a noble ligand compound having two metal centers and a spacer connecting the metal centers into which a divalent functional group having a heteroatom is introduced.

It is another aspect of the present invention to provide a noble organic chromium compound.

It is still another aspect of the present invention to provide a catalyst system for ethylene oligomerization, having excellent catalytic activity, and particularly having high selective distribution to 1-hexene or 1-octene.

It is still another aspect of the present invention to provide a method for ethylene oligomerization using the catalyst system.

Technical Solution

According to the present invention, a ligand compound represented by the following Chemical Formula 1 is provided.

[Chemical Formula 1]

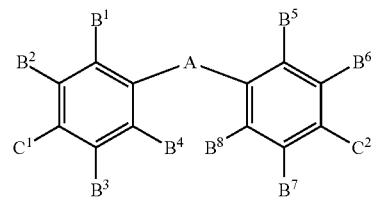

In Chemical Formula 1,

A is a divalent functional group having a heteroatom, $B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group, and $C^1$ and $C^2$ are independently hydrogen or —$N[X(R^3R^4)]_2$, wherein at least one of $C^1$ and $C^2$ is —$N[X(R^3R^4)]_2$, N is nitrogen, X is independently phosphorus (P), arsenic (As), or antimony (Sb), and $R^3$ and $R^4$ are independently a hydrocarbyl group or a heterohydrocarbyl group.

Further, according to the present invention, an organic chromium compound represented by the following Chemical Formula 2 is provided.

[Chemical Formula 2]

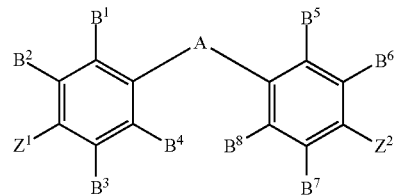

In Chemical Formula 2,

A is a divalent functional group having a heteroatom;

$B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group; and $Z^1$ and $Z^2$ are independently hydrogen or a group represented by the following Chemical Formula 3, wherein at least one of $Z^1$ and $Z^2$ is the group represented by the following Chemical Formula 3.

[Chemical Formula 3]

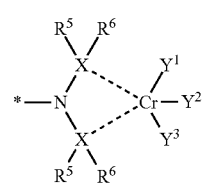

In Chemical Formula 3,

N is nitrogen,

X is independently phosphorus (P), arsenic (As), or antimony (Sb), $R^5$ and $R^6$ are independently a hydrocarbyl group or a heterohydrocarbyl group, Cr is chromium, and $Y^1$, $Y^2$, and $Y^3$ are independently a halogen, hydrogen, or a $C_1$-$C_4$ hydrocarbyl group.

Furthermore, according to the present invention, a catalyst system for ethylene oligomerization, including the ligand compound represented by Chemical Formula 1 and a source of chromium, or the organic chromium compound represented by Chemical Formula 2; and a cocatalyst is provided.

Furthermore, according to the present invention, a method for ethylene oligomerization, including the step of carrying out a polymerization reaction in the presence of the catalyst system for forming an alpha-olefin, is provided.

Advantageous Effects

The catalyst system for ethylene oligomerization according to the present invention not only has excellent catalytic activity but also shows more improved liquid olefin selectivity, and enables more effective preparation of an alpha-olefin through the oligomerization of ethylene particularly because it is possible to control the selectivity to 1-hexene or 1-octene.

DETAILED DESCRIPTION OF THE EMBODIMENTS

Hereinafter, the ligand compound, the organic chromium compound, the catalyst system for ethylene oligomerization, and the method for ethylene oligomerization using the same according to the embodiments of the preparation invention are explained in more detail.

Technical terms in the present specification are only for mentioning specific embodiments, and they are not intended to restrict the present invention unless there is a particular mention about them. The singular expressions used herein may include the plural expressions unless they are differently expressed contextually. The meaning of the term "include" used in the specification embodies specific characteristics, areas, essences, steps, actions, elements, and/or components, and does not exclude existence or addition of other specific characteristics, areas, essences, steps, actions, elements, components, and/or groups.

n the present specification, 'catalyst system' means what can be obtained as the catalyst composition having activity by mixing 3 components including chromium (or a source of the same), a ligand compound, and a cocatalyst, or alternatively 2 components of an organic chromium compound and a cocatalyst, at the same time or in an arbitrary order. Said 3 components or 2 components of the catalyst system may be mixed in the presence or absence of a proper solvent and a monomer, and it may be used in the form of being supported or unsupported.

Ligand Compound

According to one embodiment of the invention, the ligand compound represented by the following Chemical Formula 1 is provided.

[Chemical Formula 1]

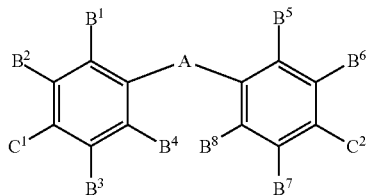

In Chemical Formula 1,

A is a divalent functional group having a heteroatom;

$B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group; and $C^1$ and $C^2$ are independently hydrogen or $-N[X(R^3R^4)]_2$, wherein at least one of $C^1$ and $C^2$ is $-N[X(R^3R^4)]_2$, N is nitrogen, X is independently phosphorus (P), arsenic (As), or antimony (Sb), and $R^3$ and $R^4$ are independently a hydrocarbyl group or a heterohydrocarbyl group.

As the result of successive experiments of the present inventors, it is recognized that the catalyst system for ethylene oligomerization including the ligand compound represented by Chemical Formula 1 not only has excellent catalytic activity but also shows more improved liquid olefin selectivity, and particularly enables more effective preparation of an alpha-olefin through the oligomerization of ethylene because it is possible to control the selectivity to 1-hexene or 1-octene.

The ligand compound represented by Chemical Formula 1 includes two metal centers and a spacer for reducing the interaction of the metal centers.

Particularly, the spacer of the ligand compound includes a divalent functional group having a heteroatom introduced therein. Since the divalent functional group having the heteroatom may act as an electron withdrawing group or an electron donating group, the electron density in the compound can be variously controlled.

Furthermore, the steric hindrance effect of the ligand compound may be controlled by controlling the number of the substituents at the ortho-aryl position. The ligand compound of the embodiment shows not only high catalytic activity to the oligomerization reaction of ethylene but also more improved liquid olefin selectivity, and particularly enables more effective preparation of an alpha-olefin because it is possible to control the selectivity to 1-hexene or 1-octene by controlling the electron density and the steric hindrance effect.

In the embodiment of the invention, A in Chemical Formula 1 is a divalent functional group having a heteroatom. Here, the heteroatom may be a halogen atom, sulfur, nitrogen, or oxygen. Specifically, according to one embodiment, A may be $-O-$, $-C=N-$, $-C(O)-$, or $-C(R^1R^2)-$, wherein at least one of $R^1$ and $R^2$ may be a $C_1$-$C_6$ halogenated alkyl group, sulfonic acid group ($-SO_3H$), or ammonia group ($-NH_3^+$), and the rest may be hydrogen. The halogenated alkyl group is an alkyl group of which at least one hydrogen is substituted by a halogen, and said substitution may be a single substitution or a plural substitution.

In this way, as the divalent functional group having the heteroatom (an electron withdrawing group or an electron donating group) is introduced into A in Chemical Formula 1, the electron density in the compound can be variously controlled as necessary, and thus it is possible to provide the ligand compound which has excellent catalytic activity and in which it is easy to control the selectivity to 1-hexene or 1-octene.

Meanwhile, according to the embodiment of the invention, $B^1$, $B^2$, $B^3$, $B^4$, $B^5$, $B^6$, $B^7$, and $B^8$ in Chemical Formula 1 may independently be hydrogen, a hydrocarbyl group, or a heterohydrocarbyl group. Preferably, $B^1$, $B^2$, $B^3$, $B^4$, $B^5$, $B^6$, $B^7$, and $B^8$ in Chemical Formula 1 may independently be hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group. Here, at least one hydrogen included in the alkyl group, the cycloalkyl group, the aryl group, the aralkyl group, and the alkoxy group may be substituted with a $C_1$-$C_{10}$ alkyl group, a $C_1$-$C_{10}$ alkoxy group, a halogen group, or a cyano group.

$C^1$ and $C^2$ in Chemical Formula 1 may independently be hydrogen or —$N[X(R^3R^4)]_2$, wherein at least one of $C^1$ and $C^2$ may be —$N[X(R^3R^4)]_2$.

N is nitrogen in —$N[X(R^3R^4)]_2$, and X may independently be phosphorus (P), arsenic (As), or antimony (Sb), and preferably it may be phosphorus (P), respectively.

Furthermore, $R^3$ and $R^4$ may independently be a hydrocarbyl group or a heterohydrocarbyl group. As a nonrestrictive example, $R^3$ and $R^4$ may independently be a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group.

Here, at least one hydrogen included in the alkyl group, the cycloalkyl group, the aryl group, the aralkyl group, and the alkoxy group may be substituted with a $C_1$-$C_{10}$ alkyl group, a $C_1$-$C_{10}$ alkoxy group, a halogen group, or a cyano group. Preferably, $R^3$ and $R^4$ may independently be a methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, cumyl, mesityl, biphenyl, naphthyl, anthracenyl, methoxy, ethoxy, phenoxy, tolyloxy, dimethylamino, thiomethyl, or trimethylsilyl group.

Particularly, in the embodiment of the invention, at least one of $C^1$ and $C^2$ may be —$N[P(C_6H_5)_2]_2$.

For a nonrestrictive example, the ligand compound represented by Chemical Formula 1 may be the compounds represented by C-01 to C-02 in examples disclosed later. However, the ligand compound of the embodiment may be realized by various combinations in the range of Chemical Formula 1 in addition to the compound of the examples. And the ligand compound represented by Chemical Formula 1 may be synthesized by applying known reactions, and the details about the synthesis method will be disclosed in the examples.

Organic Chromium Compound

According to another embodiment of the invention, an organic chromium compound represented by the following Chemical Formula 2 is provided.

[Chemical Formula 2]

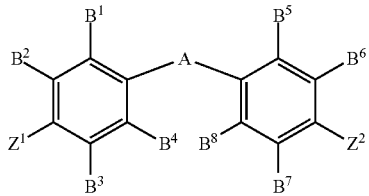

In Chemical Formula 2,
A is a divalent functional group having a heteroatom;
$B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group; and $Z^1$ and $Z^2$ are independently hydrogen or a group represented by the following Chemical Formula 3, wherein at least one of $Z^1$ and $Z^2$ is a group represented by the following Chemical Formula 3.

[Chemical Formula 3]

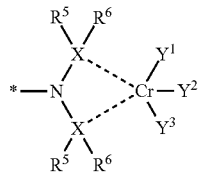

In Chemical Formula 3,
N is nitrogen,
X is independently phosphorus (P), arsenic (As) or antimony (Sb),
$R^5$ and $R^6$ are independently a hydrocarbyl group or a heterohydrocarbyl group,
Cr is chromium, and
$Y^1$, $Y^2$, and $Y^3$ are independently a halogen, hydrogen, or a $C_1$-$C_4$ hydrocarbyl group.

The organic chromium compound represented by Chemical Formula 2 is a chromium complex compound of the ligand compound represented by Chemical Formula 1. That is, the organic chromium compound may have a structure in which at least one of —$N[X(R^3R^4)]_2$ groups introduced into the ligand compound of Chemical Formula 1 forms a coordinate bond with chromium or the source of chromium.

Here, details and concrete examples about A, $B^1$, $B^2$, $B^3$, $B^4$, $B^5$, $B^6$, $B^7$, and $B^8$ in Chemical Formula 2 are the same as explained in Chemical Formula According to one embodiment, $Z^1$ and $Z^2$ in Chemical Formula 2 are independently hydrogen or the group represented by Chemical Formula 3, wherein at least one of $Z^1$ and $Z^2$ is the group represented by Chemical Formula 3.

In the group represented by Chemical Formula 3, N is nitrogen, and X may be phosphorus (P), arsenic (As), or antimony (Sb), and preferably it may be phosphorus (P), respectively.

Furthermore, $R^5$ and $R^6$ in Chemical Formula 3 may independently be a hydrocarbyl group or a heterohydrocarbyl group. As nonrestrictive examples, $R^5$ and $R^6$ may independently be a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group.

Here, at least one hydrogen included in the alkyl group, the cycloalkyl group, the aryl group, the aralkyl group, and the alkoxy group may be substituted with a $C_1$-$C_{10}$ alkyl group, a $C_1$-$C_{10}$ alkoxy group, a halogen group, or a cyano group. Preferably, $R^5$ and $R^6$ may independently be a methyl, ethyl, propyl, propenyl, propynyl, butyl, cyclohexyl, 2-methylcyclohexyl, 2-ethylcyclohexyl, 2-isopropylcyclohexyl, benzyl, phenyl, tolyl, xylyl, o-methylphenyl, o-ethylphenyl, o-isopropylphenyl, o-t-butylphenyl, o-methoxyphenyl, o-isopropoxyphenyl, cumyl, mesityl, biphenyl, naphthyl, anthracenyl, methoxy, ethoxy, phenoxy, tolyloxy, dimethylamino, thiomethyl, or trimethylsilyl group.

Meanwhile, Cr is chromium in Chemical Formula 3, and $Y^1$, $Y^2$, and $Y^3$ are independently a halogen, hydrogen, or a $C_1$-$C_4$ hydrocarbyl group.

The organic chromium compound of Chemical Formula 2 may be synthesized by a common method for preparing the ligand compound of Chemical Formula 1.

The organic chromium compound of Chemical Formula 2 may be used for oligomerization reaction of ethylene, and can have excellent catalytic activity and high selectivity distribution to 1-hexene and/or 1-octene.

Catalyst System for Ethylene Oligomerization

According to still another embodiment of the invention, a catalyst system for ethylene oligomerization, including:
 i) the ligand compound represented by the following Chemical Formula 1 and a source of chromium, or ii) the organic chromium compound represented by the following Chemical Formula 2; and
 a cocatalyst
is provided.

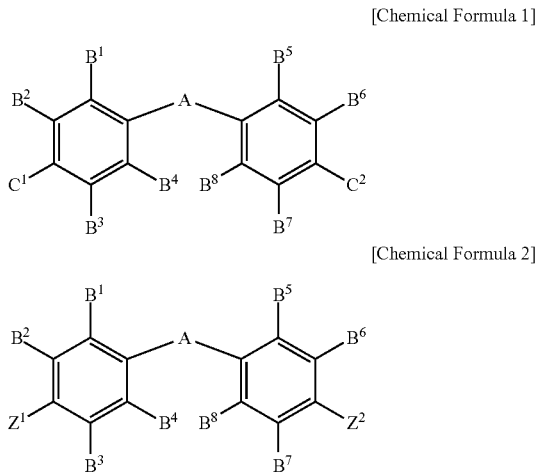

[Chemical Formula 1]

[Chemical Formula 2]

In Chemical Formulae 1 and 2,

A is a divalent functional group having a heteroatom;

$B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group;

$C^1$ and $C^2$ are independently hydrogen or —N[X($R^3R^4$)]$_2$, wherein at least one of $C^1$ and $C^2$ is —N[X($R^3R^4$)]$_2$, N is nitrogen, X is independently phosphorus (P), arsenic (As), or antimony (Sb), and $R^3$ and $R^4$ are independently a hydrocarbyl group or a heterohydrocarbyl group; and $Z^1$ and $Z^2$ are independently hydrogen or the group represented by the following Chemical Formula 3, wherein at least one of $Z^1$ and $Z^2$ is the group represented by the following Chemical Formula 3.

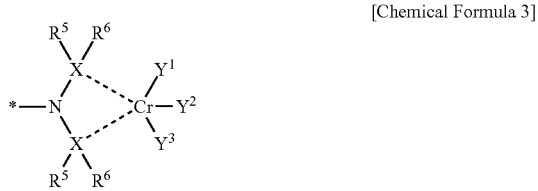

[Chemical Formula 3]

In Chemical Formula 3,

N is nitrogen,

X is phosphorus (P), arsenic (As), or antimony (Sb), $R^5$ and $R^6$ are independently a hydrocarbyl group or a heterohydrocarbyl group, Cr is chromium, and $Y^1$, $Y^2$, and $Y^3$ are independently a halogen, hydrogen, or a $C_1$-$C_4$ hydrocarbyl group.

Details and concrete examples about A, $B^1$, $B^2$, $B^3$, $B^4$, $B^5$, $B^6$, $B^7$, $B^8$, $C^1$, $C^2$, $Z^1$, and $Z^2$ in Chemical Formulae 1 and 2 are the same as disclosed above.

According to one embodiment, the catalyst system may be i) a tricomponent catalyst system including the ligand compound represented by Chemical Formula 1, a source of chromium, and a cocatalyst, and according to another embodiment, the catalyst system may be ii) a bicomponent catalyst system including the organic chromium compound represented by Chemical Formula 2 and a cocatalyst.

The source of chromium is chromium or a chromium precursor, and as a nonrestrictive example, it may be a compound which can form the organic chromium compound represented by Chemical Formula 2 by a coordinate bond with the ligand compound represented by Chemical Formula 1. According to one embodiment, the source of chromium may be one or more compounds selected from the group consisting of chromium(III)acetylacetonate, trichloro tris (tetrahydrofuran) chromium, and chromium(III)-2-ethylhexanoate.

Meanwhile, the catalyst system of one embodiment includes a cocatalyst.

The cocatalyst is an organic metal compound including a Group 13 metal, and any compound which can be used for polymerizing an olefin in the presence of a catalyst of a transition metal compound may be unlimitedly applied to the present invention.

According to one embodiment, the cocatalyst may be one or more compounds selected from the group consisting of the compounds represented by the following Chemical Formulae 4 to 6.

$$—[Al(R^7)—O]_c—$$ [Chemical Formula 4]

In Chemical Formula 4, each $R^7$ is the same as or different from each other and are independently a halogen radical, a $C_1$-$C_{20}$ hydrocarbyl radical, or a $C_1$-$C_{20}$ hydrocarbyl radical substituted with a halogen, and c is an integer of 2 or more.

$$D(R^8)_3$$ [Chemical Formula 5]

In Chemical Formula 5,

D is aluminum or boron, and $R^8$ is a $C_1$-$C_{20}$ hydrocarbyl or a $C_1$-$C_{20}$ hydrocarbyl substituted with a halogen.

$$[L-H]^+[Q(E)_4]^-$$ [Chemical Formula 6]

In Chemical Formula 6,

L is a neutral Lewis base, $[L-H]^+$ is a Bronsted acid, Q is boron or aluminum of a +3 oxidation state, and E is independently a $C_6$-$C_{20}$ aryl group or a $C_1$-$C_{20}$ alkyl group of which at least one hydrogen is substituted with a halogen, a $C_1$-$C_{20}$ hydrocarbyl, an alkoxy functional group, or a phenoxy functional group.

According to one embodiment, the compound represented by Chemical Formula 4 may be an alkyl aluminoxane such as methyl aluminoxane, ethyl aluminoxane, isobutyl aluminoxane, butyl aluminoxane, and the like.

According to one embodiment, the compound represented by Chemical Formula 5 may be trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, and so on.

Furthermore, according to one embodiment, the compound represented by Chemical Formula 6 may be triethylammonium tetraphenylborate, tributylammonium tetraphenylborate, trimethylammonium tetraphenylborate, tripropylammonium tetraphenylborate, trimethylammonium tetra(p-tolyl)borate, tripropylammonium tetra(p-tolyl)borate, triethylammonium tetra(o,p-dimethylphenyl)borate, trimethylammonium tetra(o,p-dimethylphenyl)borate, tributylammonium tetra(p-trifluoromethylphenyl)borate, trimethylammonium tetra(p-trifluoromethylphenyl)borate, tributylammonium tetrapentafluorophenylborate, N,N-diethylanilinium tetraphenylborate, N,N-diethylanilinium tetraphenylborate, N,N-diethylanilinium tetrapentafluorophenylborate, diethylammonium tetrapentafluorophenylborate, triphenylphosphonium tetraphenylborate, trimethylphosphonium tetraphenylborate, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylborate, triphenylcarbonium tetraphenylaluminum, triphenylcarbonium tetra(p-trifluoromethylphenyl)borate, triphenylcarbonium tetrapentafluorophenylborate, and so on.

The content ratio of the components composing the catalyst system may be determined by considering the catalytic activity and the selectivity to linear alpha-olefins. According to one embodiment, when the catalyst system is a tricomponent catalyst system, it is preferable that the mole ratio of the ligand compound to the source of chromium to the cocatalyst is controlled to be about 1:1:1 to 10:1:10,000, or about 1:1:100 to 5:1:3,000. According to one embodiment, when the catalyst system is a bicomponent catalyst system, it is preferable that the mole ratio of the organic chromium compound to the cocatalyst is controlled to be 1:1 to 1:10,000, or 1:1 to 1:5000, or 1:1 to 1:3000.

The components composing the catalyst system may be mixed at the same time or in an arbitrary order in the presence or absence of a proper solvent and a monomer for acting as an active catalyst system. The proper solvent may be heptane, toluene, 1-hexene, diethylether, tetrahydrofuran, acetonitrile, dichloromethane, chloroform, chlorobenzene, methanol, acetone, and so on.

Furthermore, according to one embodiment, the catalyst system may further include a supporting material. That is, the ligand compound of Chemical Formula 1 may be applied to the oligomerization of ethylene in the form of being supported on the supporting material. The supporting material may be metals, metal salts, or metal oxides which are commonly applied to a supported catalyst. For nonrestrictive examples, the supporting material may be silica, silica-alumina, silica-magnesia, and so on, and may include an oxide, a carbonate, a sulfate, or a nitrate component such as $Na_2O$, $K_2CO_3$, $BaSO_4$, $Mg(NO_3)_2$, and so on.

Oligomerization Method of Ethylene Using the Catalyst System

According to still another embodiment of the invention, a method for ethylene oligomerization, including the step of carrying out the oligomerization reaction of ethylene in the presence of the catalyst system for forming an alpha-olefin, is provided.

The method for oligomerization of ethylene of the present invention may be carried out by applying said catalyst system and a common device and contact technology. For nonrestrictive examples, the oligomerization reaction of ethylene may be carried out by a homogeneous liquid phase reaction in the presence or absence of an inert solvent, by a slurry reaction using the catalyst system that is partially or not totally dissolved, by a bulk reaction in which the alpha-olefin, the product, acts as a main medium, or by a gas phase reaction.

The oligomerization reaction of ethylene may be carried out in the presence of an inert solvent. For nonrestrictive examples, the inert solvent may be benzene, toluene, xylene, cumene, heptane, cyclohexane, methylcyclohexane, methylcyclopentane, n-hexane, 1-hexene, 1-octene, and so on.

The oligomerization reaction of ethylene may be carried out at a temperature of about 0 to 200° C., about 0 to 150° C., about 30 to 100° C., or about 50 to 100° C. Furthermore, the reaction may be carried out at a pressure of about 15 to 1500 psig, about 15 to 1000 psig, or about 15 to 700 psig.

In this was, when the oligomerization reaction of ethylene is carried out by using the catalyst system, high selectivity distribution to 1-hexene and/or 1-octene is shown and it is possible to prepare linear alpha-olefins more effectively.

Hereinafter, preferable examples and comparative examples are presented for better understanding the present invention. However, the following examples are only for illustrating the present invention and the present invention is not limited to or by them.

EXAMPLE 1

(Synthesis of Ligand Compound)

A refined methylene chloride solution in which about 1.0 g (about 4.9 mol) of 4,4'-diaminodiphenylether and about 4 ml (about 40.8 mmol) of triethylamine(triethylamine) were dissolved was prepared under an argon atmosphere at room temperature.

About 2.1 ml (about 11.1 mmol) of chlorodiphenylphosphine was slowly added dropwise to the solution. After stirring the mixture for a day, the prepared salt was eliminated therefrom. An excess of triethyl amine and chlorodiphenylphosphine was eliminated therefrom by vacuum drying the filtered solution, and a white solid of Compound C-01 (yield: about 99.9%) was obtained therefrom.

[Compound C-01]

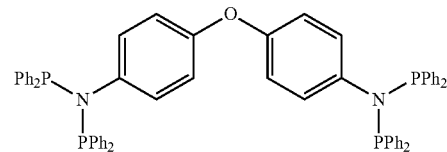

NMR spectrum of Compound C-01 is as follows.

$^1$H NMR (CDCl$_3$, standard material TMS) δ (ppm): 6.39-6.41(4H, d, ArH), 6.47-6.49 (4H, d, ArH), 7.27-7.35 (40H, m, ArH)

$^{16}$C NMR (CDCl$_4$, 25° C.) δ (ppm): 118.26, 127.97-128.03 (t), 130.25, 133.13-135.35 (t), 139.14-139.27 (t), 142.31, 154.51

$^{61}$P NMR (CDCl$_6$) δ (ppm): 70.4 (s)

EXAMPLE 2

(Synthesis of Ligand Compound)

Compound C-02 (yield: about 98.9%) was obtained according to the same method as in Example 1, except that 2,2-bis(4-aminophenyl)hexafluoropropane was used instead of 4,4'-diaminodiphenylether.

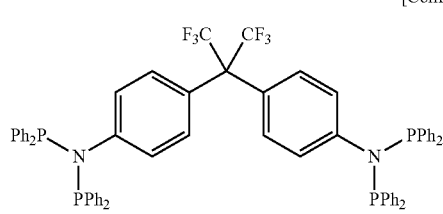

[Compound C-02]

NMR spectrum of Compound C-02 is as follows.

$^1$H NMR (CDCl$_3$, standard material TMS) δ (ppm): 6.63-6.65 (4H, d, ArH), 6.74-6.76 (4H, ArH), 7.23-7.28 (16H, m, ArH), 7.36-7.39 (24H, m, ArH)

$^{16}$C NMR (CDCl$_4$, 25° C.) δ (ppm): 63.5-67.9 (m), 127.4-127.5 (t), 127.9-128.0 (t), 128.3-128.5 (q), 129.1 (s), 130.0 (s), 132.9-133.1 (t), 135.1-135.4 (dd), 138.7-138.8 (t), 148 (5)

$^{61}$P NMR (CDCl$_6$) δ (ppm): 69.4 (s)

COMPARATIVE EXAMPLE 1

(Synthesis of Ligand Compound)

Compound D-01 (yield: about 97.8%) was obtained according to the same method as in Example 1, except that 4,4'-diaminodiphenylmethane was used instead of 4,4'-diaminodiphenylether.

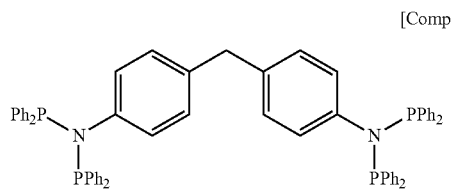

[Compound D-01]

NMR spectrum of Compound D-01 is as follows.

$^1$H NMR (CDCl$_3$, standard material TMS) δ (ppm): 3.61 (2H, s, CH$_2$), 6.48-6.49 (4H, d, ArH), 6.57-6.59 (4H, d, ArH), 7.22-7.40 (40H, m, ArH)

$^{16}$C NMR (CDCl$_4$, 25° C.) δ (ppm): 40.44 (CH$_2$), 127.89-127.95 (t), 128.61, 128.76-128.95 (t), 129.38, 133.08-133.31 (t), 138.04, 139.29-139.24 (t), 145.26

$^{61}$P NMR (CDCl$_6$) δ (ppm): 69.5 (s)

COMPARATIVE EXAMPLE 2

(Synthesis of Ligand Compound)

Compound D-02 (yield: about 96.9%) was obtained according to the same method as in Example 1, except that 4,4'-methylenebis(2-methylaniline) was used instead of 4,4'-diaminodiphenylether.

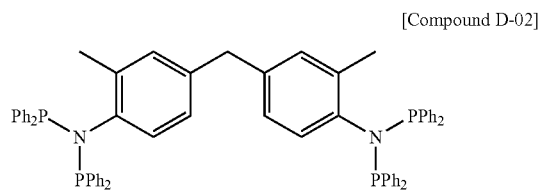

[Compound D-02]

NMR spectrum of Compound D-02 is as follows.

$^1$H NMR (CDCl$_3$, standard material TMS) δ (ppm): 1.64 (6H, s, CH$_3$), 3.74 (2H, s, CH$_2$), 6.59-6.60 (2H, d, ArH), 6.61-6.62 (2H, d, ArH), 6.80 (2H, s, ArH), 7.19-7.30 (40H, m, ArH)

$^{16}$C NMR (CDCl$_4$, 25° C.) δ (ppm): 19.3 (s), 40.4 (s), 114.8 (s), 124.1 (s), 128.2 (s), 128.3-128.4 (d), 128.4 (s), 129.0 (s), 130.9 (s), 131.1 (s), 135.1-135.4 (dd), 145.0 (s).

$^{61}$P NMR (CDCl$_6$) δ (ppm): 62.0 (s)

PREPARATION EXAMPLE 1

An autoclave with a 2 L capacity and which was dried for a day under vacuum and at a temperature of 160° C. was prepared. About 60 ml of refined toluene and about 10 ml of methylaluminoxane (MAO) were introduced into the autoclave.

After introducing a solution prepared by dissolving about 20 μmol of Compound C-01 of Example 1 in about 10 ml toluene solution and a solution prepared by dissolving tris(tetrahydrofuran)trichloridochromium (III) (Cr(THF)$_3$Cl$_3$) in toluene into a Schlenk flask and stirring the same at room temperature for about 10 min, the mixed solution was introduced into the autoclave.

Successively, the solution was stirred for activation for about 5 min, ethylene gas at 30 atm was injected into the autoclave, and the reaction was carried out for 60 min by operating a mechanical stirrer at 500 rpm.

After the reaction, the temperature was reduced to about 10° C. and the gas inside the container was vented out. About 1 ml of nonane was added thereto as the internal standard for GC-FID analysis, and the mixture was stirred for about 5 min. After taking a small quantity of the product and quenching the same by injecting HCl/EtOH therein, MAO and HCl were eliminated by adding water thereto. The organic layer obtained therefrom was dried with magnesium sulfate and filtered, and the mixture was analyzed with GC-FID. The remaining product was quenched with HCl/MeOH and filtered, and the amount of the solid was analyzed. The results of analysis are listed in the following Tables 1 and 2.

PREPARATION EXAMPLE 2

The oligomerization reaction of ethylene was carried out according to the same method as in Preparation Example 1, except that Compound C-02 of Example 2 was used instead of Compound C-01. The results of analysis are listed in the following Tables 1 and 2.

PREPARATION EXAMPLE 3

The oligomerization reaction of ethylene was carried out according to the same method as in Preparation Example 1, except that Compound D-01 of Comparative Example 1 was used instead of Compound C-01. The results of analysis are listed in the following Tables 1 and 2.

PREPARATION EXAMPLE 4

The oligomerization reaction of ethylene was carried out according to the same method as in Preparation Example 1, except that Compound D-02 of Comparative Example 2 was used instead of Compound C-01. The results of analysis are listed in the following Tables 1 and 2.

TABLE 1

| Preparation Example | Ligand | Activity (g · mol-cat$^{-1}$ · h$^{-1}$) | Solid content (wt %) |
|---|---|---|---|
| 1 | Example 1 | 228,720 | 5.5 |
| 2 | Example 2 | 293,230 | 8.2 |
| 3 | Comparative Example 1 | 131,300 | 13.4 |
| 4 | Comparative Example 2 | 141,620 | 14.0 |

In Table 1, the activity (g·mol-cat$^{-1}$·h$^{-1}$) means the weight of product per unit mole of ligand compound and unit time; and the solid content (wt %) means the content of solid in the product.

TABLE 2

| Preparation Example | Ligand | Liquid-phase product distribution (wt %) | | | | |
|---|---|---|---|---|---|---|
| | | $C_6$ | 1-$C_6$ in $C_6$ | $C_8$ | 1-$C_8$ in $C_8$ | 1-$C_6$ + 1-$C_8$ |
| 1 | Example 1 | 25.7 | 65.5 | 64.3 | 97.2 | 79.3 |
| 2 | Example 2 | 24.8 | 73.1 | 33.6 | 93.9 | 49.6 |
| 3 | Comparative Example 1 | 25.9 | 53.8 | 60.6 | 94.1 | 70.9 |
| 4 | Comparative Example 2 | 24.4 | 78.6 | 28.1 | 88.1 | 43.9 |

In Table 2, $C_6$ is the content of the product having 6 carbons in the liquid-phase product, and the content of 1-hexene in the same is expressed as 1-$C_6$ in $C_6$; and $C_8$ is the content of the product having 8 carbons in the liquid-phase product, and the content of 1-octene in the same is expressed as 1-$C_8$ in $C_8$.

As shown in Tables 1 and 2, the ligand compound of Example 1 in which the electron donating functional group is introduced shows relatively high selectivity to 1-hexene and 1-octene in comparison to the case of applying the compound of Comparative Example 1 or 2 to the oligomerization reaction of ethylene.

Further, the ligand compound of Example 2 in which the electron withdrawing functional group is introduced shows relatively low selectivity to 1-hexene and 1-octene. In this way, the electron density in the compound can be variously controlled as necessary by introducing the divalent functional group having a heteroatom into the spacer of the ligand compound having two metal centers. Further, it is recognized that the selectivity to 1-hexene and 1-octene can be easily controlled in the oligomerization reaction of ethylene.

The invention claimed is:

1. A ligand compound represented by the following Chemical Formula 1:

[Chemical Formula 1]

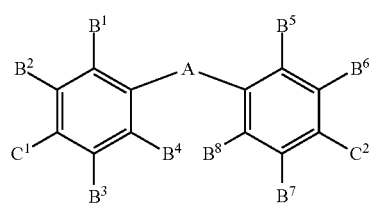

in Chemical Formula 1,
A is —O—, —C═N—, —C(O)—, or —C(R$^1$R$^2$)—, and at least one of R$^1$ and R$^2$ is a C$_1$-C$_6$ halogenated alkyl group, sulfonic acid group (—SO$_3$H), or ammonia group (—NH$_3^+$) and the rest are hydrogen;
B$^1$, B$^2$, B$^3$, B$^4$, B$^5$, B$^6$, B$^7$, and B$^8$ are independently hydrogen, a substituted or unsubstituted C$_1$-C$_{10}$ alkyl group, a substituted or unsubstituted C$_4$-C$_{10}$ cycloalkyl group, a substituted or unsubstituted C$_6$-C$_{15}$ aryl group, a substituted or unsubstituted C$_7$-C$_{15}$ aralkyl group, or a substituted or unsubstituted C$_1$-C$_{10}$ alkoxy group; and
C$^1$ and C$^2$ are independently hydrogen or —N[X(R$^3$R$^4$)]$_2$, wherein at least one of C$^1$ and C$^2$ is —N[X(R$^3$R$^4$)]$_2$, N is nitrogen, X is independently phosphorus (P), arsenic (As), or antimony (Sb), and R$^3$ and R$^4$ are independently a hydrocarbyl group or a heterohydrocarbyl group.

2. The ligand compound according to claim 1, wherein the heteroatom is a halogen atom, sulfur, nitrogen, or oxygen.

3. The ligand compound according to claim 1, wherein R$^3$ and R$^4$ are independently a substituted or unsubstituted C$_1$-C$_{10}$ alkyl group, a substituted or unsubstituted C$_4$-C$_{10}$ cycloalkyl group, a substituted or unsubstituted C$_6$-C$_{15}$ aryl group, a substituted or unsubstituted C$_7$-C$_{15}$ aralkyl group, or a substituted or unsubstituted C$_1$-C$_{10}$ alkoxy group.

4. The ligand compound according to claim 1, wherein at least one of C$^1$ and C$^2$ is —N[P(C$_6$H$_5$)$_2$]$_2$.

5. An organic chromium compound, represented by the following Chemical Formula 2:

[Chemical Formula 2]

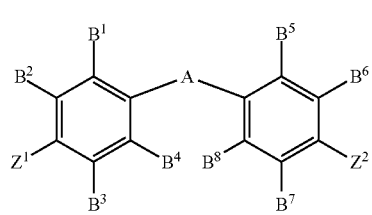

in Chemical Formula 2,
A is a divalent functional group having a heteroatom;
B$^1$, B$^2$, B$^3$, B$^4$, B$^5$, B$^6$, B$^7$, and B$^8$ are independently hydrogen, a substituted or unsubstituted C$_1$-C$_{10}$ alkyl group, a substituted or unsubstituted C$_4$C$_{10}$ cycloalkyl group, a substituted or unsubstituted C$_6$-C$_{15}$ aryl group, a substituted or unsubstituted C$_7$-C$_{15}$ aralkyl group, or a substituted or unsubstituted C$_1$-C$_{10}$ alkoxy group; and
Z$^1$ and Z$^2$ are independently hydrogen or a group represented by the following Chemical Formula 3, wherein at least one of $Z^1$ and $Z^2$ is the group represented by the following Chemical Formula 3:

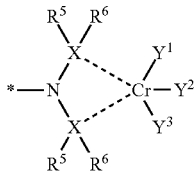

[Chemical Formula 3]

in Chemical Formula 3,
N is nitrogen,
X is independently phosphorus (P), arsenic (As), or antimony (Sb),
$R^5$ and $R^6$ are independently a hydrocarbyl group or a heterohydrocarbyl group,
Cr is chromium, and
$Y^1$, $Y^2$, and $Y^3$ are independently a halogen, hydrogen, or a $C_1$-$C_4$ hydrocarbyl group.

6. The organic chromium compound according to claim 5, wherein the heteroatom is a halogen atom, sulfur, nitrogen, or oxygen.

7. The organic chromium compound according to claim 5, wherein A is —O—, —C═N—, —C(O)—, or —C($R^1R^2$)—, and at least one of $R^1$ and $R^2$ is a $C_1$-$C_6$ halogenated alkyl group, a sulfonic acid group (—$SO_3H$), or an ammonia group (—$NH_3^+$) and the rest are hydrogen.

8. A catalyst system for ethylene oligomerization, including:
i) a ligand compound represented by the following Chemical Formula 1 and a source of chromium, or ii) an organic chromium compound represented by the following Chemical Formula 2; and
a cocatalyst:

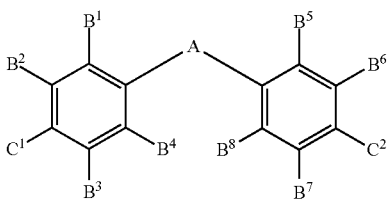

[Chemical Formula 1]

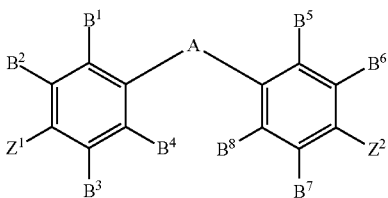

[Chemical Formula 2]

in Chemical Formulae 1 and 2,
A is a divalent functional group having a heteroatom;
$B^1$, $B^2$, $B^3$, $B^4$, $B^5$, $B^6$, $B^7$, and $B^8$ are independently hydrogen, a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group;

$C^1$ and $C^2$ are independently hydrogen or —N[X($R^3R^4$)]$_2$, wherein at least one of $C^1$ and $C^2$ is —N[X($R^3R^4$)]$_2$, N is nitrogen, X is independently phosphorus (P), arsenic (As), or antimony (Sb), and $R^3$ and $R^4$ are independently a hydrocarbyl group or a heterohydrocarbyl group; and
$Z^1$ and $Z^2$ are independently hydrogen or the group represented by the following Chemical Formula 3, wherein at least one of $Z^1$ and $Z^2$ is the group represented by the following Chemical Formula 3:

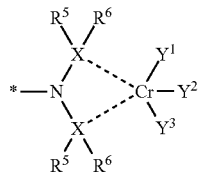

[Chemical Formula 3]

in Chemical Formula 3,
N is nitrogen,
X is phosphorus (P), arsenic (As), or antimony (Sb),
$R^5$ and $R^6$ are independently a hydrocarbyl group or a heterohydrocarbyl group,
Cr is chromium, and
$Y^1$, $Y^2$, and $Y^3$ are independently a halogen, hydrogen, or a $C_1$-$C_4$ hydrocarbyl group.

9. The catalyst system for ethylene oligomerization according to claim 8, wherein the heteroatom is a halogen atom, sulfur, nitrogen, or oxygen.

10. The catalyst system for ethylene oligomerization according to claims 8, wherein A is —O—, —C═N—, —C(O)—, or —C($R^1R^2$)—, and at least one of $R^1$ and $R^2$ is a $C_1$-$C_6$ halogenated alkyl group, a sulfonic acid group (—$SO_3H$), or an ammonia group (—$NH_3^+$) and the rest are hydrogen.

11. The catalyst system for ethylene oligomerization according to claim 8, wherein $R^3$, $R^4$, $R^5$, and $R^6$ are independently a substituted or unsubstituted $C_1$-$C_{10}$ alkyl group, a substituted or unsubstituted $C_4$-$C_{10}$ cycloalkyl group, a substituted or unsubstituted $C_6$-$C_{15}$ aryl group, a substituted or unsubstituted $C_7$-$C_{15}$ aralkyl group, or a substituted or unsubstituted $C_1$-$C_{10}$ alkoxy group.

12. The catalyst system for ethylene oligomerization according to claim 8, wherein at least one of $C^1$ and $C^2$ is —N[P($C_6H_5$)$_2$]$_2$.

13. The catalyst system for ethylene oligomerization according to claim 8, wherein the source of chromium is one or more compounds selected from the group consisting of chromium(III)acetylacetonate, trichloro tris(tetrahydrofuran) chromium, and chromium(III)-2-ethylhexanoate.

14. The catalyst system for ethylene oligomerization according to claim 8, wherein the cocatalyst is one or more compounds selected from the group consisting of the compounds represented by the following Chemical Formulae 4 to 6:

—[Al($R^7$)—O]$_c$—    [Chemical Formula 4]

in Chemical Formula 4,
each $R^7$ is same as or different from each other and are independently a halogen radical, a $C_1$-$C_{20}$ hydrocarbyl radical, or a $C_1$-$C_{20}$ hydrocarbyl radical substituted with a halogen, and c is an integer of 2 or more, D($R^8$)$_3$    [Chemical Formula 5]

in Chemical Formula 5,

D is aluminum or boron, and $R^8$ is a $C_1$-$C_{20}$ hydrocarbyl or a $C_1$-$C_{20}$ hydrocarbyl substituted with a halogen, $$[L-H]^+[Q(E)_4]^- \qquad \text{[Chemical Formula 6]}$$

in Chemical Formula 6,

L is a neutral Lewis base, $[L-H]^+$ is a Bronsted acid, Q is boron or aluminum of a +3 oxidation state, and E is independently a $C_6$-$C_{20}$ aryl group or a $C_1$-$C_{20}$ alkyl group of which at least one hydrogen is substituted with a halogen, a $C_1$-$C_{20}$ hydrocarbyl, an alkoxy functional group, or a phenoxy functional group.

15. A method for ethylene oligomerization, including the step of carrying out a polymerization reaction in the presence of the catalyst system according to claim 8.

* * * * *